United States Patent [19]

Willer

[11] Patent Number: 4,503,229

[45] Date of Patent: Mar. 5, 1985

[54] 1,4,5,8-TETRANITRO-1,4,5,8-TETRAAZADIFURAZANO-[3,4-c][3,4-H]DECALIN

[75] Inventor: Rodney L. Willer, Ridgecrest, Calif.

[73] Assignee: United States of America as represented by the Secretary of the Navy, Washington, D.C.

[21] Appl. No.: 507,444

[22] Filed: Jun. 24, 1983

[51] Int. Cl.³ .................................... C07D 498/22
[52] U.S. Cl. .................................. 544/343; 544/350; 149/92
[58] Field of Search ........................... 544/343, 350

[56] References Cited

U.S. PATENT DOCUMENTS 4,443,602  4/1984  Willer .................................. 544/350

OTHER PUBLICATIONS

Willer, Report NWC-TP-6303, SBI-AD-EYS0017, Order No. AD-A116666 NTIS (1981).

*Primary Examiner*—Robert Gerstl
*Attorney, Agent, or Firm*—R. F. Beers; W. Thom Skeer; Thomas W. Hennen

[57] ABSTRACT

A novel explosive compound, 1,4,5,8-tetranitro-1,4,5,8-tetraazadifurazano[3,4-c][3,4-h]decalin is prepared by the reaction of 3,4-diaminofurazan and glyoxal in dilute hydrochloric acid, followed by the nitration of the intermediate 1,4,5,8-tetraazadifurazano[3,4-c][3,4-h]decalin. The nitrated compound has a higher density and detonation pressure and velocity than the known explosives HMX and HNB.

2 Claims, No Drawings

1,4,5,8-TETRANITRO-1,4,5,8-TETRAAZADIFURAZANO-[3,4-c][3,4-H]DECALIN

BACKGROUND OF THE INVENTION

1. Field of the Invention

This invention relates to the preparation of a polynitramine compound. More particularly, this invention relates to a high density, high energy polynitramine.

2. Description of the Prior Art 1,3,5,7-tetranitro-1,3,5,7-tetraazacyclooctane (HMX) is currently the most powerful explosive in use. HMX has a density of 1.90 g/cc and a detonation pressure of 393 kbar. Hexanitrobenzene (HNB) is one of the most powerful explosives known with a measured density of 2.01 g/cc and a measured detonation pressure of 406 kbar.

SUMMARY OF THE INVENTION 1,4,5,8-tetranitro-1,4,5,8-tetraazadifurazano[3,4-c][3,4-h]decalin is a highly energetic compound. It has been calculated to be a more powerful explosive compound than HMX or HNB. The compound is prepared by the reaction of 3,4-diaminofurazan and glyoxal followed by nitration.

An object of this invention is to provide a novel explosive compound.

Other objects and novel features of the invention will become apparent from the following detailed description.

DESCRIPTION OF THE PREFERRED EMBODIMENT

The synthesis of 1,4,5,8-tetranitro-1,4,5,8-tetraazadifurazano-[3,4-c][3,4-h]decalin involved the reaction of 3,4-diaminofurazan and glyoxal in dilute hydrochloric acid to obtain the compound 1,4,5,8-tetraazadifurazano-[3,4-c][3,4-h]decalin, followed by nitration to yield the final product.

3,4-diaminofurazan was prepared following the procedure of Carmark and coworkers, J. Org. Chem., v. 40, 2752 (1975). The procedure involved the dehydration of the known diaminoglyoximine with an aqueous base.

The following examples illustrate the process of preparing the novel compound without restricting it to what is described therein.

EXAMPLE I

A 10 gram portion (0.1 mole) of 3,4-diaminofurazan was added to a solution of 10 g of 37% hydrochloric acid in 20 ml of distilled water. This slurry was stirred at 60° C. while 7.25 g of 40% aqueous glyoxal was added. The mixture was stirred for one additional hour and then cooled. The product, 1,4,5,8-tetraazadifurazano [3,4-c][3,4-h]decalin, was collected and washed well with water. After drying, it weighed 10.86 g (0.049 moles, 98% yield). The material can be recrystallized from 50:50 DMF/H$_2$O to give plates with a melting point of 230°–231° C.

Analysis calculated for $C_6H_6N_8O_2$: C, 32.43; H, 2.72; N, 50.44. Found: C, 32.26; H, 2.74; N, 50.19.

EXAMPLE 2

A magnetic stirring bar and 14 ml of trifluoroacetic anhydride were placed into a 100 ml round-bottom flask. After cooling to −5° C. (salt-ice bath), 6.0 ml of 100% nitric acid was added dropwise, with stirring, over a period of 20 minutes. This mixture was allowed to warm briefly to room temperature. Then, it was recooled and 2.22 g of 1,4,5,8-tetraazadifurazano[3,4-c][3,4-h]decalin was added in small portions over a period of 10 minutes. The mixture was allowed to slowly come to room temperature over 4 hours. The product, 1,4,5,8-tetranitro-1,4,5,8-tetraazadifurazano-[3,4-c][3,4-h]decalin, was collected by vacuum filtration under a blanket of nitrogen and washed well with methylene chloride. The last traces of solvent were removed under vacuum. The compound can be recrystallized by dissolving it in 100% nitric acid and adding an equal volume of trifluoroacetic acid, followed by cooling.

It has been noted that the compound 1,4,5,8-tetranitro-1,4,5,8-tetraazadifurazano[3,4-c][3,4-h]decalin is somewhat thermally unstable. Samples of the material left standing at room temperature, soon emit a red gas. Upon prolonged standing, the material turns gummy. It is believed that this decomposition might be due to the presence of trace amounts of acid; however, even recrystallized material shows this behavior.

The low thermal stability of the compound made the determination of its physical and chemical properties very difficult. The density was determined to be greater than 1.987 g/cc because crystals of the material sink in 1,3-dibromopropane (d=1.987 g/cc). The heat of formation was measured to be +185 kcal/mole by the standard technique of back calculation from the heat of combustion. This should be considered a minimum value for the heat of formation since some time elapsed between weighing the samples and the combustion.

From the heat of formation and the density, a detonation pressure of 419 kbar and a detonation velocity of 9.43 mm/us were calculated using the method of Kamlet and Jacobs, J. of Chem. Physics, v. 48, 23–35 (1968). The impact sensitivity was measured to be 20 cm on a Model 12 impact machine (2.5 kg drop weight).

Obviously, many modifications and variations of the present invention are possible in light of the above teachings. It is therefore to be understood that, within the scope of the appended claims, the invention may be practiced otherwise than as specifically described.

What is claimed is:
1. 1,4,5,8-tetranitro-1,4,5,8-tetraazadifurazano[3,4-c][3,4-h]-decalin.
2. 1,4,5,8-tetraazadifurazano[3,4-c][3,4-h]decalin.